United States Patent [19]

Scott

[11] Patent Number: 5,270,189

[45] Date of Patent: Dec. 14, 1993

[54] BIPARTICLE FLUIDIZED BED REACTOR
[75] Inventor: Charles D. Scott, Oak Ridge, Tenn.
[73] Assignee: Martin Marietta Energy Systems, Inc., Oak Ridge, Tenn.
[21] Appl. No.: 798,856
[22] Filed: Nov. 21, 1991

Related U.S. Application Data

[63] Continuation of Ser. No. 548,176, Jul. 3, 1990, abandoned.
[51] Int. Cl.$^5$ .............................................. C12P 7/56
[52] U.S. Cl. .................................. 435/139; 422/140; 422/147; 435/182; 435/288; 435/803; 435/813; 562/589
[58] Field of Search ............... 422/140, 141, 145, 147; 435/139, 311, 313, 316, 803, 813, 182, 288, 176–180; 562/580, 589

[56] References Cited

U.S. PATENT DOCUMENTS

| | | | |
|---|---|---|---|
| 2,907,389 | 10/1959 | Hitzman | 166/8 |
| 3,520,067 | 7/1970 | Winegartner | 34/9 |
| 3,646,689 | 3/1972 | Kuchenthal et al. | 422/145 X |
| 3,761,393 | 9/1973 | Wolk et al. | 208/108 |
| 3,966,599 | 6/1976 | Burkhead | 210/14 |
| 4,048,018 | 9/1977 | Coughlin et al. | 435/813 |
| 4,094,767 | 6/1978 | Gifford, II | 208/11 R |
| 4,419,330 | 12/1983 | Ishihara et al. | 422/145 X |
| 4,431,509 | 2/1984 | Tarman | 208/8 R |
| 4,433,978 | 2/1984 | Schenone et al. | 422/145 |
| 4,450,294 | 5/1984 | Feldman | 562/608 |
| 4,578,176 | 3/1986 | Tarman | 208/8 R |
| 4,618,418 | 10/1986 | Heijnen et al. | 422/140 |
| 4,665,027 | 5/1987 | Dale et al. | 435/813 |
| 4,746,615 | 5/1988 | Buchholz et al. | 435/313 |
| 4,842,719 | 6/1989 | MacAurthur et al. | 208/421 |
| 4,846,964 | 7/1989 | Scott et al. | 208/428 |
| 4,978,616 | 12/1990 | Dean, Jr. et al. | 435/813 |
| 5,068,419 | 11/1991 | Kulprathipanja et al. | 562/580 |
| 5,093,085 | 3/1992 | Engstrom et al. | 422/145 X |

OTHER PUBLICATIONS

B. H. Davison et al., "Operability and Feasibility of Ethanol Production by Immobilized *Zymomonas mobilis* in a Fluidized-Bed Bioreactor", *Applied Biochemistry and Biotechnology*, vol. 18, pp. 19–34 (1988).
H. Y. Wang, "Integrating Biochemical Separation and Purification Steps in Fermentation Processes", *Annals New York Academy Sciences*, vol. 413, pp. 313–321 (1983).
S. S. Lee et al., "Repeated Fed-Batch Fermentation Using Yeast Cells and Activated Carbon Extraction System", *Biotechnology and Bioengineering Symposium*, No. 12, pp. 221–231 (1982).
G. T. Frank, et al., "An Integrated Bioreactor-Separator: In Situ Recovery of Fermentation Products by a Novel Membrane-Based Dispersion-Free Solvent Extraction Technique", *Biotechnology and Bioengineering Symposium*, No. 17, pp. 303–316 (1986).
R. M. Busche, et al., "Technoeconomics of Butanol Extractive Fermentation in a Multiphase Fluidized Bed Bioreactor", *Applied Biochemistry and Biotechnology*, vol. 20/21, pp. 357–374 (1989).
C. D. Scott, "Techniques for Producing Monodispersed Biocatalyst Beads for Use in Columnar Reactors", *Annals of the New York Academy of Sciences*, vol. 501, pp. 487–493.
B. H. Davison, "Dispersion and Holdup in a Three-Phase Fluidized Red Reactor", *Applied Biochemistry and Biotechnology*, vol. 20/21, pp. 449–460 (1989).
C. D. Scott et al., "Solute Diffusion in Biocatalyst Gel Beads Containing Biocatalysts and Other Additives", *Enzyme Microb. Technol.*, vol. 11, pp. 258–263 (1989).
W. W. Pitt, et al., "Recovery of Ethanol from Fermentation Broths Using Selective Sorption-Desorption", *Biotechnology and Bioengineering*, vol. XXV, pp. 123–131 (1983).

Primary Examiner—James C. Housel
Assistant Examiner—Amalia Santiago
Attorney, Agent, or Firm—L. L. Ericson; J. A. Marasco; P. H. Smirman

[57] ABSTRACT

A fluidized bed reactor system which utilizes a fluid phase, a retained fluidized primary particulate phase, and a migratory second particulate phase. The primary particulate phase is a particle such as a gel bead containing an immobilized biocatalyst. The secondary particulate phase, continuously introduced and removed in either cocurrent or countercurrent mode, acts in a secondary role such as a sorbent to continuously remove a product or by-product constituent from the fluid phase. Introduction and removal of the sorbent phase is accomplished through the use of feed screw mechanisms and multivane slurry valves.

7 Claims, 3 Drawing Sheets

BIPARTICLE FLUIDIZED BED REACTOR

The U.S. Government has rights in this invention pursuant to Contract Number DE-AC05-84OR21400 with Martin Marietta Energy Systems, Inc., awarded by the U.S. Department of Energy and funded through the Energy Conversion and Utilization Technologies (ECUT) Program.

CROSS-REFERENCE TO RELATED APPLICATIONS

This application is a continuation of application Ser. No. 07/548,176 filed Jul. 3, 1990, now abandoned.

FIELD OF THE INVENTION

The invention relates to multiphase fluidized bed reactors, and more particularly to fluidized bed reactors which employ a fluidizing medium, a retained particulate phase, and one or more nonretained particulate phases.

BACKGROUND OF THE INVENTION

Conventional fluidized bed type reactors operate as a columnar chamber through which there is an upflow of a fluid that suspends or fluidizes particles into an expanded bed. The particulates tend to migrate throughout the bed, usually at a slow rate, but they are contained within the bed while the fluid progresses through the suspended particles as essentially a front or in "plug flow." The particulates are typically catalysts such as biocatalyst beads, or feed material such as coal. The fluid phase (gas, liquid, or a mixture of the two) is typically a feed material or reactant at the reactor inlet, and a product and/or waste material at the reactor outlet.

For some applications, it is desirable to have means for continuously removing a product constituent from the fluid phase. This would be particularly useful in fluidized bed bioreactors where the retained particulates are immobilized biocatalysts that may be inhibited by the build-up of the product concentration.

Fluidized bed reactors have been used in the chemical process industry for many years, and such reactors utilizing immobilized biocatalysts have been studied for continuous fermentation and other bioreactor applications. A high productivity ethanol fermentation in an immobilized-cell fluidized-bed bioreactor has been demonstrated as disclosed in B. H. Davison and C. D. Scott, *Applied Biochemistry and Biotechnology*, Vol. 18, p. 19 (1988). Other uses for fluidized bed bioreactors are disclosed in U.S. Pat. No. 4,846,964, issued on Jul. 11, 1989. Although reactor systems, particularly bioreactors, may already operate with three phases (gas, liquid, solid), it has been suggested by H. Y. Wang, *Annals New York Academy Sciences*, Vol. 413, p. 313 (1983), that the addition of a separations agent (sorbent or solvent) may also be useful so that the conversion and separation step can be carried out simultaneously. It has been disclosed by S. S. Lee and H. Y. Wang, *Biotechnology and Bioengineering Symposium*, No. 12, p. 221 (1982), that solid sorbents can be added to stirred-tank reactors. Solvents can be used to extract product in membrane reactors, as disclosed by G. T. Frank and K. K. Sirkar, *Biotechnology and Bioengineering Symposium*. No. 17, p. 303 (1986). Another process which utilizes liquid product extraction technology is taught by R. M. Busche, et al, *Applied Biochemistry and Biotechnology*, Vol. 20/21, p. 357 (1989). Since many possible organic solvents are also toxic or inhibitory to microorganisms or enzymes, the use of continuous solvent extraction in fluidized bed bioreactor systems does not appear to be generally useful.

Methods for preparing gel beads useful in carrying out the present invention are found in C. D. Scott, *Annals of the New York Academy of Sciences*, Vol. 501, p. 487 (1987). Further work discussing fundamental hydrodynamics is disclosed by B. H. Davison, *Applied Biochemistry and Biotechnology*, Vol. 20/21, p. 449 (1989). Still further work which discusses biocatalyst bead properties is found in C. D. Scott, et al., *Enzyme Microb. Technol.*, Vol. 11, p. 258 (1989).

OBJECTS OF THE INVENTION

Accordingly, it is an object of the present invention to provide a new and improved fluidized bed reactor system having a flowing fluid first phase, a retained particulate second phase, and a particulate third phase which is continuously introduced into and removed from the reactor.

It is another object of the invention to provide means for removing product and/or by-product from a fluidized bed reactor process, eliminating inhibitory effects thereof on the process.

It is a further object of the invention to provide a fluidized bed reactor system which can be operated at high rates of efficiency.

Further and other objects of the present invention will become apparent to the skilled artisan upon the reading of the specification.

SUMMARY OF THE INVENTION

In accordance with one aspect of the present invention, a new and improved fluidized bed reactor system comprises a fluidized bed type reactor vessel; a fluid first phase which flows through the reactor vessel; a fluidized particulate second phase in the reactor vessel which is retained therein; and a fluidized particulate third phase in the reactor vessel which migrates through the reactor vessel.

Another aspect of the invention is a fluidized bed reactor system which comprises a fluidized bed type reactor vessel having a fluid inlet, a fluid outlet, introducing means for introducing particulate material, and removing means for removing particulate material; a fluid first phase flowing through the inlet, upwardly through the reactor vessel, and thence through the outlet; a fluidized particulate second phase retained within the reactor vessel; and a fluidized particulate third phase which is introduced into the reactor vessel by the introducing means, migrates through the vessel, and then is removed from the reactor vessel by the removing means.

Another aspect of the invention is a countercurrent mode fluidized bed reactor system, which comprises a fluidized bed type reactor vessel having an upper region and a lower region; a fluid inlet connected to the lower region; a fluid outlet connected to the upper region; introducing means connected to upper region for introducing downwardly migratory particulate material; and removing means connected to the lower region for removing downwardly migratory particulate material.

A further aspect of the present invention is a cocurrent mode fluidized bed reactor system, which comprises a fluidized bed type reactor vessel having an upper region and a lower region; a fluid inlet connected to the lower region; a fluid outlet connected to the upper region; introducing means connected to the lower region for introducing upwardly migratory particulate material; and removing means connected to the upper region for removing upwardly migratory particulate material.

A further aspect of the invention is a simultaneously countercurrent and cocurrent mode fluidized bed reactor system, which comprises a fluidized bed type reactor vessel having an upper region and a lower region; a fluid inlet connected to the lower region; a fluid outlet connected to the upper region; first introducing means connected to the upper region for introducing downwardly migratory particulate material; first removing means connected to the lower region for removing downwardly migratory particulate material; second introducing means connected to the lower region for introducing upwardly migratory particulate material; and second removing means connected to the upper region for removing upwardly migratory particulate material.

Figure 1:
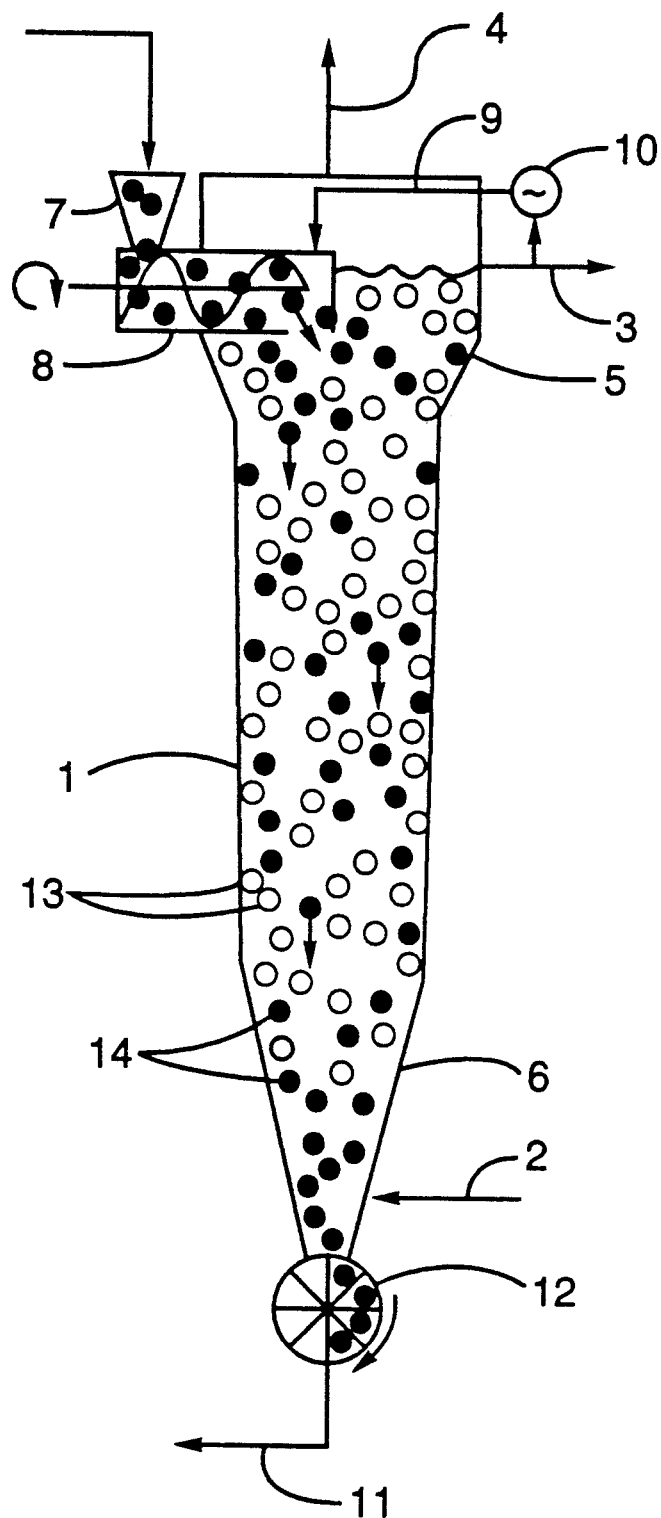
FIG. 1 is a schematic drawing of a biparticle fluidized bed reactor system operating in countercurrent mode. Secondary particles having a higher settling velocity than the primary particles are introduced at the top by a feed screw mechanism and removed at the bottom by a rotating multivane particulate removal valve mechanism.

For a better understanding of the present invention, together with other and further objects, advantages, and capabilities thereof, reference is made to the following disclosure and appended claims in connection with the above-described drawings.

DETAILED DESCRIPTION OF THE PREFERRED EMBODIMENTS

Particles in a fluidized bed reactor have general mobility within the bed after the fluid phase is introduced at a rate sufficient to separate or suspend the particles in the flow field. This suspended bed of particles generally remains in the reactor unless the settling velocities of the particles are sufficiently small so that they are swept out, or unless a large additional volume of particulates is introduced which surpasses the capacity of the reactor.

The present invention is based on serendipitous observations that in such a system with a range of particle sizes and/or densities, especially where there is a liquid continuous phase, there is ultimately a segregation of the particles with the lighter and/or smaller particles, which have a lower settling velocity, generally in the top portion of the bed of suspended particles and the larger and/or more dense particles, which have a higher settling velocity generally in the bottom portion. The term biparticle, as applied to the present invention, is intended to define a system which contains two kinds of particles which differ in settling velocity sufficiently to separate under fluidization. The term triparticle, as applied to the present invention, is intended to define a system which contains three kinds of particles, each of which differ in settling velocity sufficiently to separate under fluidization.

Among the unique features of the invention are included the use of a fluidized bed reactor, with primary particles, in a suspended or fluidized state while secondary particles, with different physical properties, are introduced at the top of the reactor and removed at the bottom after migrating through the fluidized bed countercurrent to the upflow of the fluid phase, and/or they are introduced at the bottom of the reactor and removed at the top of the reactor after migrating through the fluidized bed cocurrently with the upflow of the fluid phase. Unique apparatus, including means for introducing and removing the secondary particles are also described.

Consider now a fluidized bed reactor system having an upflowing fluid phase which fluidizes a primary particulate phase composed of primary particles which generally remain in the reactor vessel. When another particulate phase composed of secondary particles having a settling velocity different from the settling velocity of the primary particles in the fluidized bed are introduced into the reactor, these secondary particles ultimately migrate to the top or the bottom of the bed. Further, when these particles are removed after their migration through the fluidized bed, a continuous operation can be carried out with the introduced particles migrating cocurrently or countercurrently with respect to the upflow of the fluid stream. The primary particles within the fluidized bed generally remain in the reactor in a generally constant zone constituting a heterogeneous continuum in which reaction occurs.

One embodiment for carrying out a process in a countercurrent mode is shown in FIG. 1 and described in detail as follows. A fluidized bed bioreactor system is employed which has conventional features such as a reactor vessel 1, a feed introduction stream 2, a liquid effluent stream 3, and an off gas stream 4. The reactor vessel has an expanded upper region 5 to enhance disengagement of gas, liquid and particles, and a tapered bottom region 6 to enhance fluid phase dispersion and allow particle separation. A primary particulate phase 13 is retained in the vessel under fluidization. A secondary particulate phase 14 is fed into the top of the reactor in a relatively dry or slurry form through a hopper 7 and a feed screw mechanism 8. The secondary particulate 14 is swept from the feed screw 8 into the top of the reactor vessel 1 by a fluid stream 9 fed from the liquid effluent stream 3 by a recycle pump 10. A secondary particulate recovery stream 11 emanates from the reactor bottom through a particulate removal valve 12, preferably a rotary type multivane or star valve.

Figure 2:
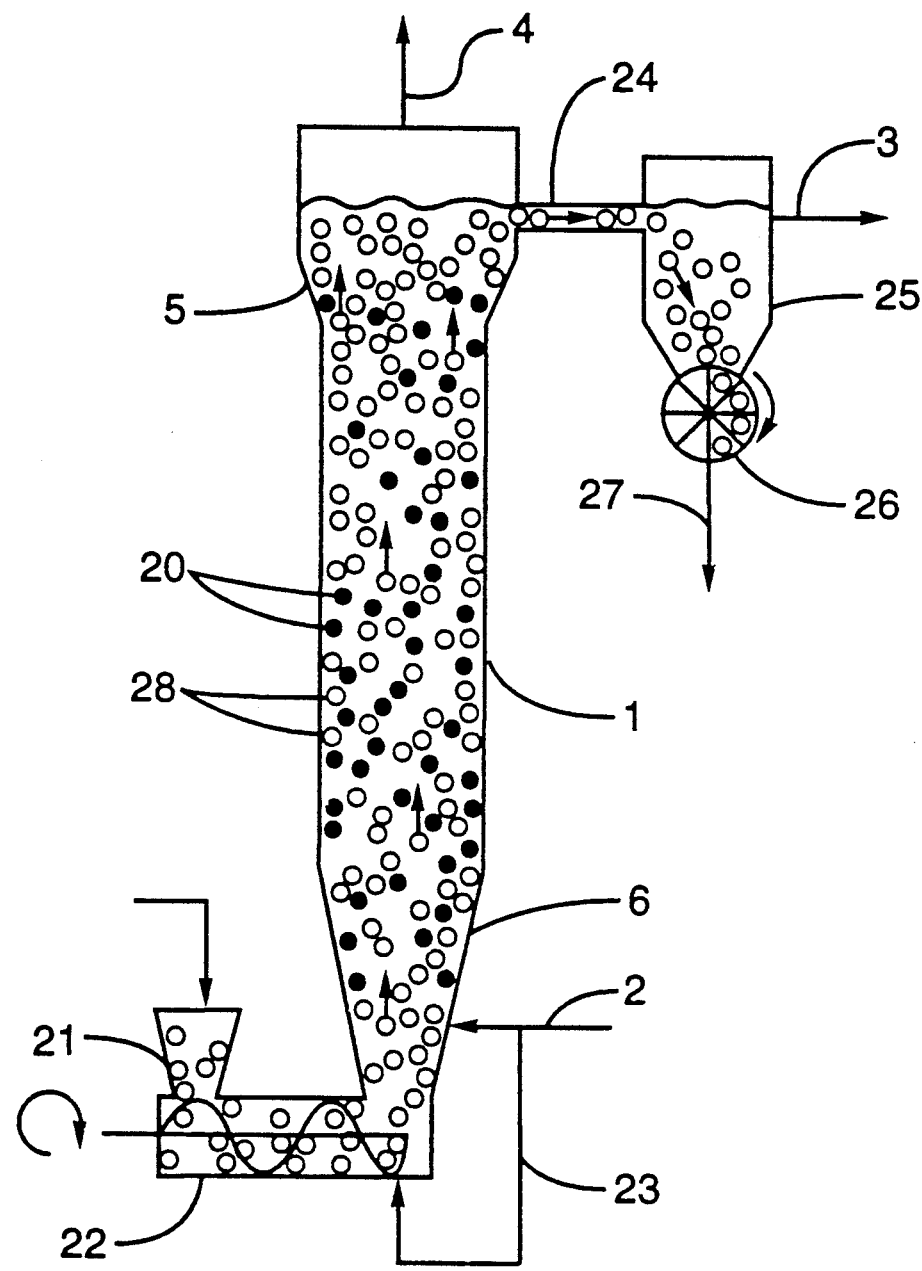
FIG. 2 is a schematic drawing of a biparticle fluidized bed reactor system operating in cocurrent mode. Secondary particles having a lower settling velocity than the primary particles are introduced at the bottom by a feed screw mechanism and removed at the top by effluent overflow and sedimentation followed by recovery through a rotating multivane particulate removal valve mechanism.

A second embodiment for carrying out a process in a cocurrent mode is shown in FIG. 2 and described in detail as follows. A fluidized bed reactor system having similar conventional elements 1-6 as described above is utilized. A primary particulate phase 20 is retained in the vessel under fluidization. A secondary particulate 28 is fed in relatively dry or slurry form through a hopper 21 and a feed screw mechanism 22 and swept into the bottom of the reactor vessel by at least a portion 23 of the feed stream 2. A slurry overflow channel 24 at the reactor top carries liquid and secondary particulate 28 to a sedimentation chamber 25 where the liquid effluent stream 3 leaves the bioreactor system. The sedimentation chamber 25 has a bottom region equipped with a multivane particulate removal rotary valve mechanism 26 from which the secondary particulate 28 is recovered through a recovery stream 27.

Figure 3:
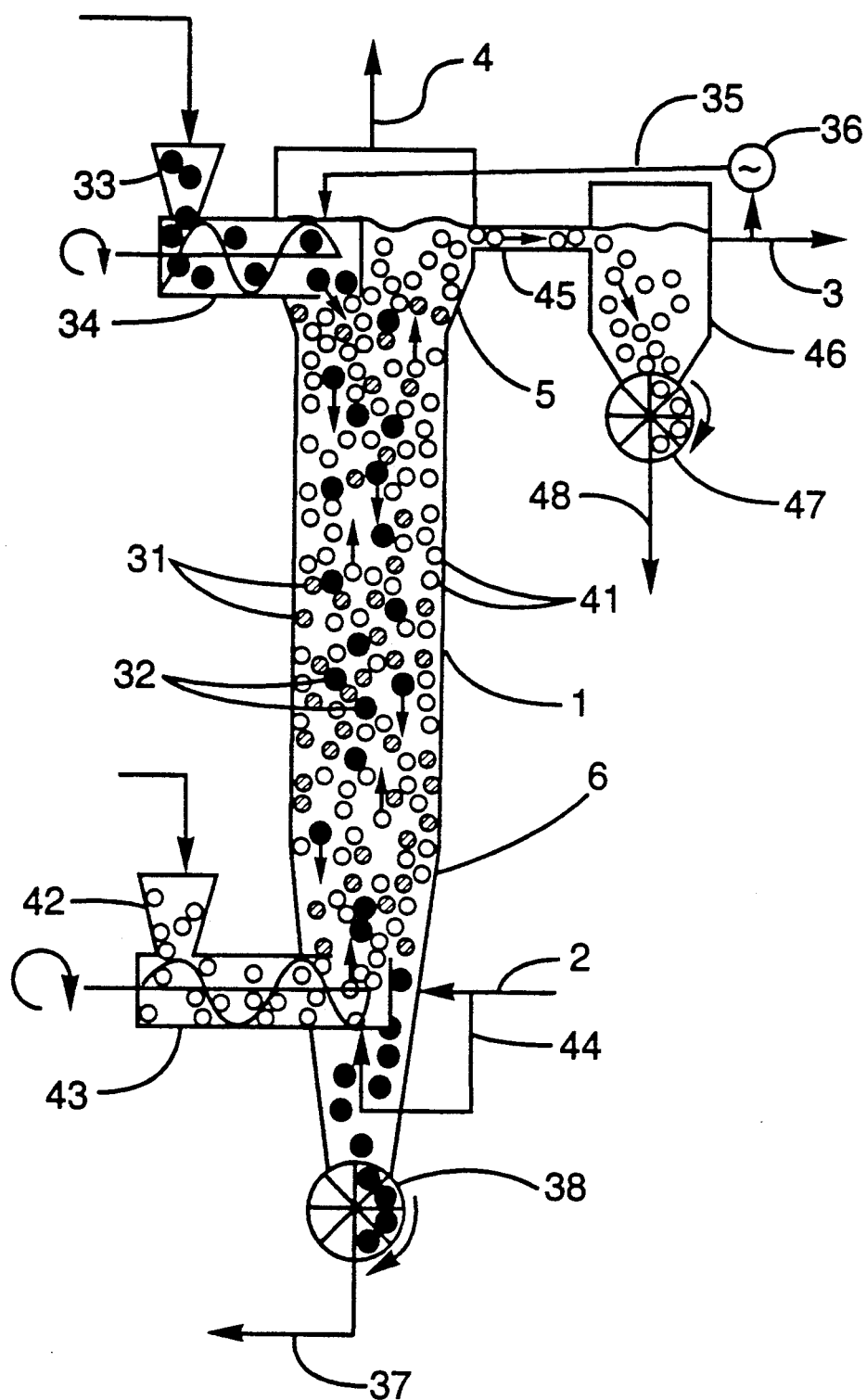
FIG. 3 is a schematic drawing of a triparticle fluidized bed reactor system operating in simultaneous countercurrent and cocurrent modes. Secondary particles having a higher settling velocity than the primary particles are introduced at the top of the reactor by a feed screw mechanism and are removed at the bottom by a rotating multivane particulate removal valve mechanism. Tertiary particles having a lower settling velocity than the primary particles are introduced at the bottom of the reactor by a feed screw mechanism and removed at the top by effluent overflow and sedimentation followed by recovery through a rotating multivane particulate removal valve mechanism.

A third embodiment for carrying out a process in a simultaneous countercurrent and cocurrent mode is shown in FIG. 3 and described in detail as follows. A fluidized bed reactor system having similar conventional elements 1-6 as described above is utilized. A primary particulate phase 31 is retained in the vessel under fluidization. A secondary particulate 32 is fed into the top of the reactor in a relatively dry or slurry form through a hopper 33 and a feed screw mechanism 34. The secondary particulate 32 is swept from the feed screw 34 into the top of the reactor vessel 1 by a fluid stream 35 fed from the liquid effluent stream 3 by a recycle pump 36. A secondary particulate recovery stream 37 emanates from the reactor bottom through a particulate removal valve 38, preferably a rotary type multivane or star valve. A tertiary particulate 41 is fed in relatively dry or slurry form through a hopper 42 and a feed screw mechanism 43 and swept into the bottom of the reactor vessel by at least a portion 44 of the feed stream 2. A slurry overflow channel 45 at the reactor top carries liquid and tertiary particulate 41 to a sedimentation chamber 46 where the liquid effluent stream 3 leaves the bioreactor system. The sedimentation chamber 46 has a bottom region equipped with a multivane particulate removal rotary valve mechanism 47 from which the tertiary particulate 41 is recovered through a recovery stream 48.

Although the preferred means for introducing and removing the secondary particulates comprise a feed screw mechanism and a rotary type multivane or star valve, additional possible means including various types of positive displacement slurry pumps, injectors, gravity feed, or any conceivable mechanism for introducing and/or removing particulates from a fluidized bed reactor are considered to be within the scope of the present invention.

EXAMPLE I

A test was made with an aqueous fluidized bed reactor system having an average inside diameter of 1.9 cm. Primary and secondary particles were prepared using crosslinked carrageenan gel that included inorganic oxides to control particle density and also to provide an identifying color. Nominal 1.5-mm-diam, essentially spherical, red colored particles containing 0.5 wt % $Fe_2O_3$ and having a specific gravity of 1.02 were used as the primary fluidized particles. Nominal 1.5-mm-diam, essentially spherical, white colored particles containing 5 wt % $CeO_2$ and having a specific gravity of 1.08 were used as the migratory, secondary particles that were introduced at the top of the column. A stable fluidized bed of the red particles 15.5 cm high was established with an average aqueous flow velocity of 0.25 cm/sec. Approximately one-half that amount of the heavier white particles was introduced at the top of the column, and the time for the white particles to migrate to the bottom of the fluidized bed with a clear interface between the two types of particles was determined. It was found that the white particles progressed countercurrently (downwardly) through the bed at a rate of approximately 0.6 cm/sec. The migration rate can be optimized by altering the liquid flow rate and/or the differences in particle size and density.

EXAMPLE II

A column about 80 cm in length and of a nominal 1" inside diameter, having a 0.5"-1" inside diameter tapered lower region and an expanded upper region of 3" inside diameter was prepared. Four symmetric liquid inlets, used in this small system to provide a uniform fluid flow, were connected to the column above the bottom region, where secondary particles were to settle and be removed. A slurry pump was connected to the upper region for introducing secondary particles. A screw-type slurry feeder is preferred for larger columns. A pump with a multivane star valve having four chambers separated by steel vanes in a teflon ring was connected to the bottom region for removing settled particulate matter. This countercurrent mode system, similar to that depicted in FIG. 1, was used in further tests of the invention.

EXAMPLE III

An experiment was carried out in the apparatus described above in Example II to study the separation and stratification of gel beads having different settling velocities. The two particle types used were both 4% k-carrageenan gel beads. The primary particles were about 1.2 mm in diameter with 3% $Fe_2O_3$ added to the composition; the secondary particles were about 1.5 mm in diameter with 5% $Ce_2O_3$ added. These beads were red and tan respectively. A bed of the red beads was fluidized in the column at a flow rate of about 125 mL/min. The red iron oxide beads became fluidized in the middle region, leaving the lower region of the column clear. The tan cerium oxide beads were then introduced into the upper region of the column. The tan beads migrated downwardly, or countercurrently, through the column and settled in the bottom region where they were removed through the star valve. The settling velocity of the tan secondary particles through the stable fluidized bed was 1.3 cm/s. This compares with a Stoke's settling velocity of 2.3 cm/s for these heavier particles.

EXAMPLE IV

The process of Example III was carried out with a gas sparger placed near the region of the inlets having a gas flow through the column at a rate of 0.1 to 1.2 liters/hour. The gas bubbles were observed to increase the mixing of the bed but did not prevent the migration or separation of secondary particles from the system.

EXAMPLE V

A co-current mode system was tested in a system similar in dimensions to that described in Example II, but having secondary particulate introducing and removing means in locations similar to that depicted in FIG. 2. Beads similar to those described in FIG. 3 were used. The heavier tan beads, now the primary particulate, were fluidized at about 11 liters/hour. A slurry of the lighter red beads was added at to the base of the column. The red beads migrated to the top of the bed and were removed.

The above examples demonstrate that the continuous contacting and separation of two different particles is possible in a fluidized bed reactor system. Further experiments were conducted to test fermentation processes for producing useful products.

EXAMPLE VI

A process using the countercurrent mode system was tested for the production of lactic acid by *Lactobacillus delbruckii*, the preferred strain being NRRL #B445. The bacteria were grown in a rich medium at about 40° C., harvested by centrifugation, washed with sterile distilled water and immobilized into small gel beads of 3% carrageenan (although 2% alginate is now considered more preferable because lighter beads are formed) using established methods. The biocatalyst beads were of a relatively uniform size of from about 0.7 to 1.2 mm diameter. These beads were the primary particulate, having a settling velocity of less than about 1 cm/s. The fermentation medium contained about 5 to 20 g/L glucose (although any suitable sugar could be used), about 5 g/L yeast extract and small amounts of salts (0.5 g/L $(NH_4)_2SO_4$, 0.3 g/L $MgSO_4$, 0.2 g/L $KH_2PO_4$ and 0.2 g/L $K_2HPO_4$) to help stabilize the pH and improve cell growth.

About 70 ml of the primary particulate phase was placed into the fluidized-bed columnar reactor described above, which was operated at 40° C. in recycle mode to maintain fluidization for these tests. A larger system would be operated with a single pass of the fluid phase. The recycle stream was passed through a uv-sterilizer to reduce contamination. Sorbent beads comprised of Reillex 425, a polyvinyl pyridine (PVP) resin, preferred because of the minimal effects of pH on its capacity, having a nominal particle size of 0.3 to 1.0 mm diameter and an estimated wet specific gravity of 1.2, were used as the secondary phase.

The second phase was added in a slurry to the top of the vessel and collected from the bottom. It was shown that the effluent lactic acid concentration could be maintained at about 0.23 g/L by sorbtion into the migratory resin particles, which sorbed the lactic acid at a concentration of about 0.06 g/L, a level not inhibitory to the fermentation process. During a three day run, the Lactobacillus bacteria concentration within the gel biocatalyst beads increased from $1.0 \times 10^{12}$ cells/L to $1.8 \times 10^{12}$ cells/L. The biocatalyst beads were also suitable for refrigeration and subsequent reactivation and reuse.

EXAMPLE VII

The sorbent resin secondary particulate phase used in the process of Example VI was regenerated by extracting the lactic acid with 1N NaOH. The amount of lactic acid recovered revealed that the overall yield of the fermentation process was 1.0 g lactate/g glucose consumed, which is the stoichiometric limit emphasizing the high efficiency and productivity of the system.

The resin used for the secondary particulate phase, as available, may have a wide size distribution which affects the fluidized stratification so that separation of the particulate phases is incomplete. Loaded sorbent within the reactor can decrease the ability of the resin to control the pH and inhibit the apparent sorption of the lactic acid. In order to improve, or optimize the particle separation in a countercurrent mode system, either the size and density of the resin can be increased, or the size or density of the biocatalyst can be decreased. In a cocurrent mode system, converse adjustments can be made to optimize the process; a simultaneously countercurrent and cocurrent mode system can be adjusted similarly to achieve optimum process conditions.

EXAMPLE VIII

The process described herein is also suitable for the enhanced production and recovery of ethanol. *Zymomonas mobilis*, a bacterium, is immobilized in 4% carrageenan beads. The feed is 15% dextrose solution made from corn syrup and light steep water with 0.05M KCl and antifoam added. In a 3-in.-ID column the flow rate is approximately 10 L/h. The optimum process temperature is about 30° to 35° C. A sorbent second particulate phase, such as a polystyrene resin or a hydrophobic molecular sieve such as Linde silicalite is added and removed continuously in accordance with the present invention to recover the ethanol product and prevent inhibitory buildup of the product in the reactor.

EXAMPLE IX

Using the novel systems and processes described herein, citric acid is produced. *Aspergillus niger* is immobilized in carrageenan gel beads for the production of citric acid from glucose. A conventional, properly formulated medium is employed to optimize citric acid production. The biocatalyst beads are fluidized in the reactor system as described above. The migratory sorbent particles, comprised of activated carbon, known to be an effective sorbent for citric acid, are continuously introduced into and removed from the system to recover the citric acid product from the process.

EXAMPLE X

Immobilized mammalian cells are used in the presently described triparticle fluidized bed reactor system as a primary particle for producing desired proteins. Monoclonal antibodies which bind specifically to a first desired protein are immobilized onto downwardly migratory secondary particles for a first product recovery. Monoclonal antibodies which bind specifically to a second desired protein are immobilized onto upwardly migratory tertiary particles for a second product recovery.

Typically, the primary particles that are retained in the fluidized bed are, but are not limited to, immobilized biocatalysts that carry out a bioconversion process on an upflowing feed stream containing a substrate. The term substrate, as used herein, is intended to define a chemical, biochemical, or biological starting material that is converted into a useful product, or otherwise acted upon in a useful process. Typical biochemical substrates can include sugars, other carbohydrates, proteins, or other biological substances, along with nutrients and/or other substances that are beneficial to a particular process. The secondary particles can be sorbents that continuously remove and concentrate the formed products or by-products, with the added advantage of reducing potential inhibitory effects of the products.

Sorbent particles such as activated carbon, various ion exchange and neutral resins, or sorbents dispersed in gel beads can be effective secondary particulates, especially in fluidized bioreactor systems. The resulting "loaded" sorbent particles removed from the reactor system can then be processed separately for recovering the concentrated product. If the recovery process is not destructive to the sorbent particles, they can be recycled and re-introduced into the reactor system to sorb more product. Furthermore, sorbent particles, in some cases, can be recycled through the reactor system several times prior to a recovery process in order to obtain a more concentrated product in or on the sorbent particles. Some resins or other sorbent particles which have good sorbing qualities for a particular process, but improper hydrodynamic properties, can be immobilized in gel beads in order to improve process hydrodynamics. W. W. Pitt et al. *Biotechnology and Bioengineering Symposium. XXV*, p. 123-131 (1983) disclose details on sorbents and extraction.

The presently disclosed fluidized bed reactor system can be applied to any process wherein solid particles can be used as a catalyst and also as a sorbent. The range of possible particle sizes can be from <100 microns to >5 mm diameter. In a biological system of immobilized cells, catalyst particles of about 0.5 to 2 mm would be typical. The minimum flow rates would be determined by the minimum fluidization velocity of the retained particles. For gel beads, the preferred superficial linear liquid velocity would be in the range of about 1 cm/min to 100 cm/min. The densities of the gel bead catalysts typically would be in the range of about 1 to 1.5 g/cc. If biocatalysts are immobilized on solid spheres (e.g., glass), the density could be up to about 4 g/cc. The sorbent densities will likely be either less than or greater than the biocatalysts, depending on the direction and rapidity of migration desired, and can be in the range of <1 up to >5 gm/cc.

The temperature and pressure can be set to the optimum for the reaction. Biocatalytic reactions usually occur from about 20° to 65° C., with 30° C. being typical, and generally are carried out at or near ambient or atmospheric pressure.

A process type of high interest is the production of chemical such as organic acids. Typical candidate acids include acetic, citric, succinic, or lactic acid. For production of these and other products, the producing microorganisms can be immobilized in uniform gel beads which are fluidized by upflow of aqueous media containing a sugar substrate and various nutrients. Denser sorbent particles can be added continuously to the top of the reactor vessel which will migrate downwardly while sorbing product, settle and be removed from the bottom of the vessel, in accordance with the countercurrent mode process.

A simultaneously countercurrent and cocurrent mode process can be carried out in a triparticle fluidized bed reactor system. Advantages of such a system include the simultaneous sorption and removal of two reaction products, or a product and a by-product. Another use of a triparticle system is the sorption of a single product by both the secondary and ternary particles to increase the efficiency of the system.

Reactor configurations are not limited to a simple colunmar shape, and introduction and removal of migratory particulates can be accomplished by other means, and can be located at various regions of a reactor. The means and locations for migratory particulate introduction and removal disclosed herein are intended to disclose the best mode of carrying out the invention.

The fluid phase can be comprised of a liquid, a gas, or a combination of liquid and gas.

The present fluidized bed reactor system can be effective as an integrated bioreactor system for various bioconversion processes important in energy production. This can include coal conversion processes wherein coal particles can comprise both the primary phase and the substrate. Also suggested are fermentation processes utilizing fluidized-bed bioreactors with immobilized biocatalyst particles that can produce ethanol and other alcohols, suitable types of organic solvents, and other organic chemicals with high-energy values.

Other possible applications include production of proteins by tissue culture cells immobilized on glass beads as a primary particle, and the continuous removal of the product protein by an antibody bound to another hydrodynamically different secondary particle. Another process can be the release of bound metals by the biodegradation of fluidized organic particulate material as a primary particle, and the capture of these metals by a resin type secondary particle. Other useful processes can involve conversion of a substrate by a primary particulate catalyst, followed by further conversion, and optionally sorption by a secondary particulate catalyst or catalyst/sorbent.

While there has been shown and described what are at present considered the preferred embodiments of the present invention, it will be obvious to the skilled artisan that various changes and modifications can be made therein without departing from the scope of the invention as defined by the appended claims.

What is claimed is:

1. A fluidized bed reactor system comprising:
   a reactor,
   primary particles inside said reactor, said primary particles having a settling velocity,
   a source of an upflowing fluidizing liquid, and
   a source of secondary particles having a settling velocity greater than said settling velocity of said primary particles,
   said reactor comprising:
     a vessel having a top portion and a bottom portion,
     a primary and secondary particle delivery means attached to said top portion of said vessel for delivery particles to said vessel,
     a primary and secondary particle removing means attached to said bottom portion of said vessel for removing primary and secondary particles from said vessel,
     an upflowing fluidizing liquid delivery means attached to said bottom portion of said vessel for delivering said upflowing fluidizing liquid to said vessel,
     an upflowing fluidizing liquid exit means attached to said top portion of said vessel for removing said upflowing fluidizing liquid from said vessel,
   said primary and secondary particle delivery means positioned to accept said secondary particles from said source of said secondary particles;
   said suspended primary particles suspended and maintained within said vessel by said upflowing fluidizing liquid flowing through said vessel, said suspended primary particles having their said settling velocity and diameters sufficient to maintain a suspended zone of said suspended primary particles within said vessel at said flow rate of said upflowing fluidizing liquid, said secondary particles having their settling velocity and diameters, said settling velocity of said secondary particles in said upflowing fluidizing liquid being greater than said settling velocity of said suspended primary particles in said upflowing fluidizing liquid, said settling velocity and said diameters of said secondary particles being sufficient to permit said secondary particles to settle to said bottom portion of said vessel through said suspended zone of said suspended primary particles; and said upflowing fluidizing liquid having a flow rate sufficient to suspend said suspended primary particles.

2. A method of operating a fluidized bed reactor system comprising the following steps:

Step 1. providing a fluidized bed reactor system comprising: a reactor, primary particles inside said reactor, said primary particles having a settling velocity, a source of an upflowing fluidizing liquid, and a source of secondary particles having a settling velocity greater than said settling velocity of said primary particles; said reactor comprising: a vessel having a top portion and a bottom portion, a primary and secondary particle delivery means attached to said top portion of said vessel, a primary and secondary particle removing means attached to said bottom portion of said vessel, an upflowing fluidizing liquid delivery means attached to said bottom portion of said vessel for delivering said upflowing fluidizing liquid to said vessel, an upflowing fluidizing liquid exit means attached to said top portion of said vessel for removing said upflowing fluidizing liquid from said vessel, said primary and secondary particle delivery means positioned to accept said secondary particles from said source of said secondary particles; said suspended primary particles being suspended and maintained within said vessel by said upflowing fluidizing liquid flowing through said vessel, said suspended primary particles having their settling velocity and diameters sufficient to maintain a suspended zone of said suspended primary particles within said vessel at said flow rate of said upflowing fluidizing liquid, said secondary particles having their settling velocity and diameters, said settling velocity of said secondary particles in said upflowing fluidizing liquid being greater that said settling velocity of said suspended primary particles in said upflowing fluidizing liquid, said settling velocity and said diameters of said secondary particles being sufficient to permit said secondary particles to settle to said bottom of said vessel through said suspended zone of said suspended primary particles; and said upflowing fluidizing liquid having a flow rate sufficient to suspend said suspended primary particles;

Step 2. continuously introducing into said reactor said secondary particles from said source of secondary particles through said primary and secondary particle delivery means attached to said top portion of said vessel;

Step 3. continuously converting said upflowing fluidizing liquid into a liquid reaction product;

Step 4. continuously removing said liquid reaction product through said liquid exit means and, Step 5. continuously removing said secondary particles which have settled from said top portion of said vessel through said suspended zone of said suspended primary particles to said bottom portion of said vessel by said primary and secondary particle removing means attached to said bottom portion of said vessel.

3. A fluidized bed reactor system in accordance with claim 1 wherein said primary and secondary particle delivery means comprises a feed screw mechanism, and said primary and secondary particle removing means comprises a particulate removal valve mechanism.

4. A fluidized bed reactor system in accordance with claim 1 wherein said upflowing fluidizing liquid comprises a reaction medium, said suspended primary particles comprise a reaction catalyst, and said secondary particles comprise a reaction product sorbent.

5. A fluidized bed reactor system in accordance with claim 4 wherein said reaction medium comprises a sugar solution, said reaction catalyst comprises a gel bead containing a microorganism that will convert said sugar solution into lactic acid, and said reaction product sorbent comprises a polyvinyl pyridine resin.

6. A method of operating a fluidized bed reactor system in accordance with claim 2 wherein said upflowing fluidizing liquid comprises a reaction medium, said suspended primary particles comprise a reaction catalyst, and said secondary particles comprise a reaction product sorbent.

7. A method of operating a fluidized bed reactor system in accordance with claim 6 wherein said reaction medium comprises a sugar solution, said reaction catalyst comprises a gel bead containing a microorganism that will convert said sugar solution into lactic acid, and said reaction product sorbent comprises a polyvinyl pyridine resin.

* * * * *